United States Patent
Wrigley et al.

(10) Patent No.: US 6,784,203 B1
(45) Date of Patent: Aug. 31, 2004

(54) CYTOKINE PRODUCTION INHIBITORS

(75) Inventors: Stephen Keith Wrigley, Slough (GB); Sangeeta Bahl, Slough (GB); Roya Mansour Sadeghi Guilani, Slough (GB); Michael Moore, Slough (GB); Werner Albert Katzer, Slough (GB); Steven Michael Martin, Slough (GB); David Andrew Kau, Slough (GB); Andrew Jonathan Whiting, Slough (GB); Neil Robinson, Slough (GB); Martin Alistair Hayes, Slough (GB); Thomas Haydn Mander, Slough (GB)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 09/284,806

(22) PCT Filed: Oct. 21, 1997

(86) PCT No.: PCT/GB97/02907

§ 371 (c)(1),
(2), (4) Date: Jun. 7, 2001

(87) PCT Pub. No.: WO98/17661

PCT Pub. Date: Apr. 30, 1998

(51) Int. Cl.[7] .................. A61K 31/335; A61K 39/00; C12P 1/02; C12P 7/00
(52) U.S. Cl. ............... 514/449; 435/171; 435/134; 435/71.1; 424/274.1
(58) Field of Search ................. 435/171, 134, 435/71.1; 424/274.1; 514/449

(56) References Cited

PUBLICATIONS

P. Wipe et al.: "Total Synthesis A. Structure Assignment of the Antitumor Aranorosin." Journal of Organic Chemistry., vol. 58, No. 25, 1993, Easton US, pp. 7195–7203, XP002052631 see p. 7195, paragraph EXPERIM. p. 7196.

A. McKillpo: "The Total Synthesis of the Diepoxycycohex-anoneantibiotic Aranorosin" Journal of the Chemical Society, Perkin Transactions 1., vol. 12, Jun. 21, 1996, Letchworth GB, pp. 1385–1392, XP002052632 see p. 1385, paragraph EXPERIM.

*Primary Examiner*—Leon B. Lankford, Jr.
*Assistant Examiner*—Ruth A. Davis

(57) ABSTRACT

A 5,6-dihydro-α-pyrone of formula (I)

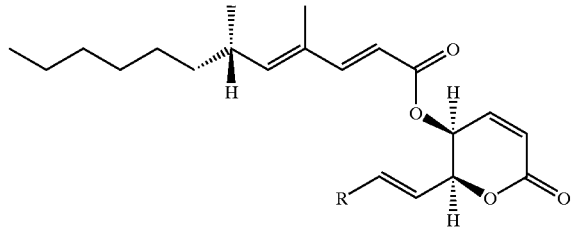

wherein R is $CO_2H$ or $CH_3$ and, when R is $CO_2H$, a pharmaceutically or veterinarily acceptable salt thereof. Processes for producing compounds of formula (I) and their use as cytokine production inhibitors.

11 Claims, No Drawings

CYTOKINE PRODUCTION INHIBITORS

The present invention relates to 5,6-dihydro-α-pyrones useful as cytokine production inhibitors, to the preparation of these compounds and to pharmaceutical and veterinary compositions containing them.

We have now discovered that fermentation of a strain of the fungus Phomopsis sp. in a nutrient medium produces two 5,6-dihydro-α-pyrones esterified in the 5-position with an unsaturated $C_{14}$ fatty acid and also the free $C_{14}$ fatty acid. We have also discovered that fermentation of a strain of the fungus Paecilomyces sp. in a nutrient medium produces a useful phomalactone.

The present invention therefore provides a 5,6-dihydro-α-pyrone of formula (I):

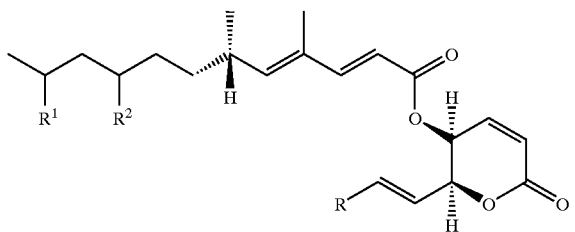

wherein R is $CO_2H$ or $CH_3$ and each of $R^1$ and $R^2$ is H; or R is $CO_2H$, one of $R^1$ and $R^2$ is H and the other is OH; or, when R is $CO_2H$, a pharmaceutically or veterinarily acceptable salt thereof.

Preferred compounds of the invention are:
3-((5S,6S)-5,6-dihydro-5-((6S)-4,6-dimethyldodeca-2E,4E-dienoyl)-2H-pyran-2-on-6-yl)-prop-2E-enoic acid; and
3-((5S,6S)-5,6-dihydro-5-((6S)-4,6-dimethyldodeca-2E,4E-dienoyl)-2H-pyran-2-on-6-yl)-prop-2E-ene.

The present invention provides a process for the preparation of a 5,6-dihydro-α-pyrone of formula (I) or a pharmaceutically or veterinarily acceptable salt thereof, which process comprises:
(i) fermenting, in a source of carbon, nitrogen and inorganic salts, fungal strain Phomopsis sp. 22502 (CBS 313.96) or a mutant thereof which produces a said 5,6-dihydro-α-pyrone;
(ii) isolating a said 5,6-dihydro-α-pyrone from the fermentation broth; and
(iii) if desired, when the isolated 5,6-dihydro-α-pyrone is the compound of formula (I) wherein R is $CO_2H$, converting the said 5,6-dihydro-α-pyrone into a pharmaceutically or veterinarily acceptable salt thereof.

The compounds of formula (I) have been isolated from a microorganism which we have designated X22502 and which has been identified as a strain of the genus Phomopsis (Saccardo) Bubák on the basis of the following morphological data with reference to the description given by SUTTON, B. C., 1980 (The Coelomycetes. Farnham Royal: Commonwealth Agricultural Bureaux):

The fungal strain Phomopsis sp. (X22502) (CBS 313.96) is a coelomycete isolated from tropical freshwater foam which produces a dense, dark grey-olivaceous (Flora of British Fungi Colour Identification Chart, 1969, Edinburgh: HMSO) mycelium with a white lobate margin at 24° C. on 2% malt extract agar with glucose and peptone (MEA: composition per liter of distilled water: Difco malt extract, 20 g; Bacto-peptone, 1 g; agar, 20 g). After 7 days the mycelium attains a diameter of 2.5–3.5 cm.

Conidiomatal development is stimulated by exposure to near-UV light. Conidiomata are solitary, carbonaceous, unilocular, ostiolate and measure 1.5–2.0 mm wide and 1.25–2.0 mm high. Conidiogenous cells are borne on branched conidiophores which line the conidiogenous cavity. These cells are hyaline, obclavate to cylindrical, integrated, phialidic and measure 16–20 μm×1.5–2.0 μm. Conidia are hyaline, aseptate and generally of three types: A-conidia (5.5–7.5 μm×1.5–3.0 μm) are ellipsoid to fusiform, usually with acute apices and a guttule at each end; B-conidia (20–32 μm×<1 μm) are hamate and filiform; C-conidia (9.5–11.5 μm×1.5–3.0 μm) are obclavate with acute apices and usually at least three guttules. All three conidial types can be found within a single conidioma. The fluvial origin and observed microscopical characters did not allow further classification to species.

The 5,6-dihydro-α-pyrones of formula (I) are associated primarily with the mycelium on termination of the fermentation. They may be recovered and purified from the medium. The separation and purification of the compounds from the fermentation broth and their recovery can be achieved using solvent extraction followed by chromatographic fractionation. The 5,6-dihydro-α-pyrone of formula (I) in which R is $CO_2H$ may be converted into pharmaceutically or veterinarily acceptable salts by conventional methods. Suitable salts include salts with alkali metals such as sodium or potassium and ammonium salts.

The 5,6-dihydro-α-pyrone of formula (I) wherein R is $CH_3$ can, alternatively, be produced by the esterification of the phomalactone of formula (II):

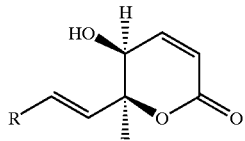

with (6S)-4,6-dimethyldodeca-2E,4E-dienoic acid which is a fatty acid of formula (IIIa):

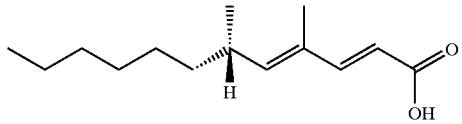

Preferably the reaction is carried out in the presence of a dehydrating agent such as DCC (dicyclohexylcarbodiimide) or EDC (1-(3-dimethylaminopropyl)-3-ethylcarbodiimide hydrochloride) and dimethylaminopyridine. The reaction is typically carried out in an inert solvent such as dichloromethane or tetrahydrofuran.

The reagents are generally mixed with stirring for example at a low temperature such as −78° C. The reaction is then allowed to warm to room temperature (20–25° C.) and stirred until complete. The reaction may be monitored chromatographically by thin layer chromatography or reversed phase high performance liquid chromatography and is typically complete within sixteen hours. Other dehydrating agents such as an alkylchloroformate and triethylamine, phenyldichlorophosphate, 2-chloro-1,3,5-trinitrobenzene and pyridine, and chlorosulphonyl isocyanate can also be used under similar conditions.

Alternatively an excess of the phomalactone of formula (II) can be reacted with the acid of formula (IIIa). The water formed can be removed by azeotropic distillation. Suitable solvents include toluene and 1,4-dioxane. The reaction is typically catalysed by acids such as sulphuric acid and ptoluenesulphonic acid.

It is advantageous to produce the 5,6-dihydro-α-pyrone of formula (I) wherein R is $CH_3$ by this route as both the phomalactone and the fatty acid can be produced by fermentation in larger quantities than the 5,6-dihydro-α-pyrone of formula (I) wherein R is $CH_3$.

The fatty acid of formula (IIIa) is one of a group of fatty acids of the following formula (III):

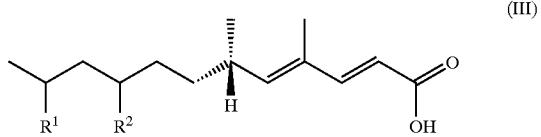

wherein one of $R^1$ and $R^2$ is H and the other is H or OH. These fatty acids can be obtained by fermentation of the fungal strain Phomopsis sp 22502 (CBS 313.96) or a mutant thereof. In accordance with the present invention, therefore, the fatty acid of formula (III) can be produced by a process which comprises:

(i) fermenting, in a source of carbon, nitrogen and inorganic salts, strain Phomopsis sp. 22502 (CBS 313.96) or a mutant thereof which produces the said fatty acid; and
(ii) isolating the said fatty acid of formula (III) from the fermentation broth.

The fatty acid of formula (III) may, of course, be isolated from the same fermentation broth as the 5,6-dihydro-α-pyrones of formula (I). The fatty acid, like the 5,6-dihydro-α-pyrones, is primarily associated with the mycelium on termination of fermentation.

Some of the fatty acids of formula (III) are novel. The present invention therefore further provides a fatty acid of formula (IIIb):

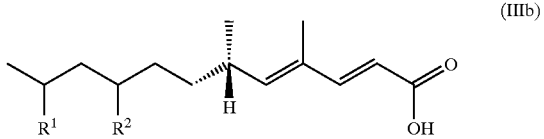

wherein one of $R^1$ and $R^2$ is H and the other is OH

The phomalactone of formula (II) can be synthesised by methods known in the prior art, for example those disclosed in Krivobok, S. et al, Pharmazie, (1994): 49, H8, 605–607; Guirand, P. et al, Pharmazie, (1994): 49, H8, 279–281; Krasnoff, S. B. et al, J. Chem. Ecol., (1994): 20, 293–302 and Murayama, T. et al, Agric. Biol. Chem., (1987): 51, 2055–2060.

The present invention does however provide a new process for the preparation of the phomalactone of formula (II), which process comprises:

(i) fermenting, in a source of carbon, nitrogen and inorganic salts, fungal strain Paecilomyces sp. 3527 (CBS 314.96) or a mutant thereof which produces the said phomalactone; and
(ii) isolating the said phomalactone from the fermentation broth.

The phomalactone is found primarily in the culture liquor on termination of the fermentation and may be recovered and purified. The separation and purification of the compound from the fermentation broth and its recovery can be achieved using solvent extraction followed by application of conventional chromatographic fractionations with various chromatographic techniques and solvent systems.

The phomalactone of formula (II) has been isolated from a microorganism which we have designated X3527 and which has been identified as a strain of the genus Paecilomyces Bainier on the basis of the following morphological data with reference to the descriptions given by SAMSON, R. A., 1974 (Paecilomyces and some allied Hyphomycetes. Studies in Mycology No. 6. Baarn: CBS). The fungal strain Paecilomyes sp. (X3527) (CBS 314.96) is an entomogenous hyphomycete isolated from a tropical Lepidoptera pupa which produces white mycelium attaining 4.5–5.0 cm diameter within 14 days at 25° C. on 2% MEA. The aerial mycelium becomes powdery as conidiogenesis occurs and may develop denser concentric zones. A pale-buff-yellow pigmentation frequently develops in aerial and/or submerged mycelium.

Conidiophores are hyaline and smooth-walled with stipe dimensions of 100–400 μm×1.5–2.5 μm and bear single or sparsely clustered phialides. Phialides are produced with the characteristic morphology of Paecilomyces Bainier measuring 7–20 μm long with a lower section inflated to 2–2.5 μm wide. The phialide neck is often considerably attenuated (<1 μm wide) and bent. Phialides of very variable morphology are also produced, e.g. lacking an inflated basal region and/or with an attenuated neck measuring about 20 μm long. Conidia are ellipsoid to cylindrical (3.5–7 μm×2–3 μm), smooth-walled, hyaline and borne in conspicuous imbricate dry chains.

Further classification as a Paecilomyces anamorph of Cordyceps (Fries) Link may be justified on the grounds of the epidopterous origin of the isolate coupled with the results of numerous studies made by H. C. Evans and R. A. Samson (unpublished data) of entomopathogenic Paecilomyces anamorphs of Cordyceps.

The strains X22502 and X3527 were deposited by Xenova Group plc of 240 Bath Road, Slough, Berkshire, SL1 4EF, United Kingdom under the Budapest Treaty at the Centraalbureau voor Schimmelcultures, Baarn, the Netherlands, on 19th Mar. 1996 under references X07/64/502 and X08/64/527 respectively. Strain X22502 was assigned the reference number CBS 313.96. Strain X3527 was assigned the reference number CBS 314.96.

The present invention also embraces mutants of the above microorganisms. For example, those which are obtained by natural selection or those produced by mutating agents including ionising radiation such as ultraviolet irradiation, or chemical mutagens such as nitrosoguanidine or the like treatments, are also included within the ambit of this invention.

The invention further provides a biologically pure culture of fungal strain X22502 or X3527 or of a mutant thereof which produces the compounds of the invention. Such cultures are substantially free from other microorganisms. The invention also provides a process for fermenting the fungal strain X22502, X3527 or a said mutant, which process comprises fermenting strain X22502 or X3527 or a said mutant thereof in a source of carbon, nitrogen and inorganic salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers' solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

An antifoam may be present to control excessive foaming and added at intervals as required.

Fermentation can be conducted at temperatures ranging from 20° C. to 40° C., preferably 24–30° C. For optimal results, it is most convenient to conduct these fermentations at a temperature in the range 24–26° C. The starting pH of the nutrient medium suitable for producing the compounds can vary from 5.0 to 8.5 with a preferred range of from 5.0 to 7.5.

Small scale fermentations are conveniently carried out by placing suitable quantities of nutrient medium in a flask by known sterile techniques, inoculating the flask with either spores or vegetative cellular growth of the fungal strain, loosely stoppering the flask with cotton wool, and permitting the fermentation to proceed in a constant room temperature of about 25° C. on a rotary shaker at from 95 to 300 rpm for 2 to 10 days. The fermentation may also be conducted in static culture on liquid or semi-solid medium.

For larger scale work, it is preferable to conduct the fermentation in suitable tanks provided with an agitator and a means of aerating the fermentation medium. The nutrient medium is made up in the tank after sterilization and is inoculated with a source of vegetative cellular growth of the fungal strain. The fermentation is allowed to continue for from 1 to 8 days while agitating and/or aerating the nutrient medium at a temperature in the range 20° C. to 37° C. The degree of aeration is dependent upon several factors such as the size of the fermenter and agitation speed. Generally the larger scale fermentations are agitated at about 95 to 750 rpm and aerations of about 0.5 to 1.5 VVM (volumes of air per volume of medium per minute).

The separation of the present compounds from the whole fermentation broth and their recovery is carried out by solvent extraction followed by application of chromatographic fractionations with various chromatographic techniques and solvent systems. The present compounds in pure form have thus been isolated in this way.

The 5,6-dihydro-α-pyrones of formula (I) and pharmaceutically and veterinarily acceptable salts of the compound of formula (I) wherein R is $CO_2H$ are inhibitors of the production of cytokines, specifically IL-1β.

These compounds can therefore be used in the treatment of disorders requiring immunosuppression, for example immunoinflammatory conditions and CNS disorders. A human or animal, e.g. a mammal, can therefore be treated by a method comprising administration of a therapeutically effective mount of a compound of formula (I), or a pharmaceutically or veterinarily acceptable salt of the compound of formula (I) wherein R is $CO_2H$.

These compounds can be used in the treatment of an immunoinflammatory condition such as rheumatoid arthritis, osteoarthritis, septic shock, psoriasis, atherosclerosis, inflammatory bowel disease, Crohn's disease and asthma. The compounds of the present invention also exhibit pharmacological properties associated with the treatment of other disorders requiring immunosuppression, for example central nervous system (CNS) disorders such as encephalomyelitis and Alzheimer's disease.

The compounds of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration for adult humans is 0.001 to 10 mg/kg, most commonly in the range of 0.01 to 5 mg/kg, body weight. Such a dosage may be given, for example, from 1 to 5 times daily orally or by bolus infusion, infusion over several hours and/or repeated administration.

The toxicity of the compounds of the invention is negligible, they can therefore safely be used in therapy.

The compounds of the present invention are formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dye-stuffs; sweeteners; wetting agents such as lecithin, polysorbates, laurylsulphates. Such preparations may be manufactured in known manner, for example by means of mixing, granulating, tabletting, sugar coating, or film coating processes.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsion may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the compounds of the present invention may be encapsulated within liposomes.

The following examples illustrate the invention

EXAMPLE 1

Batch Fermentation of Phomopsis sp. 22502

A 1.5 ml cryovial containing 1 ml of macerated vegetative mycelium suspended in a 10% glycerol solution was retrieved from storage at −135° C. A preculture was produced by aseptically placing 1 ml of starting material in a 250 ml baffled Erlenmeyer flask containing 40 ml of nutrient solution S1 and shaken at 240 rpm for 3 days at 25° C.

An intermediate culture was generated by aseptically transferring the preculture to 2 L of nutrient solution S1 in a 3 L fermenter. The fermenter was agitated at 500 rpm, aerated at 0.5 vvm, and the temperature controlled at 25° C. for 3 days.

A production culture was generated by aseptically transferring an intermediate culture to a 75 L fermenter containing 50 L of nutrient solution P1. The production fermenter was stirred at 350 rpm, aerated at 0.5 vvm, and temperature controlled at 25° C. After 5½ days incubation the fermentation was stopped and the culture was harvested.

The nutrient solutions used were as follows, percentages being by weight:

Nutrient Solution S1: 1.5% glycerol, 1.5% soya bean peptone, 1% D-glucose, 0.5% malt extract, 0.3% NaCl, 0.1% $CaCO_3$, 0.1%: Tween 80, 0.1% Junlon PW110 [suppliers: Honeywell and Stein, Sutton, Surrey, U.K.] adjusted to pH 6

Nutrient Solution P1: 3.6% molasses, 0.2% casein hydrolysate, 0.004% phytic acid, 0.09% calcium chloride, 0.1%: Tween 80, adjusted to pH 5

EXAMPLE 2

Extraction and purification of the 5,6-dihydro-α-pyrones of formula (I) wherein $R^1$ and $R^2$ are both H, and the fatty acid of formula (IIIa) from Phomopsis sp. 22502

The broth in Example 1 was harvested by filtration using a Schenk Niro 430 filter press, the clarified filtrate was discarded and the retained biomass was extracted with 25 L of recirculating methanol for 24 hours. The methanolic extract was harvested via filtration through the filter press and evaporated to an aqueous concentrate using a thin film evaporator.

The aqueous concentrate (10 L) was then back extracted with 2×7 L of an ethyl acetate:hexane (1:1) mix. The solvent extracts were pooled and evaporated to a gum under reduced pressure and redissolved in 50 ml of ethyl acetate:hexane (1:1). Purification was achieved by normal phase chromatography using a Biotage Flash 75 chromatography system and a Flash 75 KP-Sil silica (32–62 μm 60 Å) column (internal diameter (ID) 7.5×30 cm length) and an isocratic mobile phase (ethyl acetate:hexane 1:1 mix, 200 ml/min flow rate). 1 L fractions were collected and analysed by thin layer chromatography using the same mobile phase as the developing solvent.

The 5,6-dihydro-α-pyrone of formula (I) wherein R is $CO_2H$ (Rf 0.53), the 5,6-dihydro-α-pyrone of formula (I) wherein R is $CH_3$ (Rf 0.89) and the fatty acid of formula (IIIa) (Rf 0.75) rich fractions were pooled, evaporated to dryness under reduced pressure and subjected to further purification by preparative reversed phase HPLC using a Waters NovaPak C18 (100 Å 5 μM) column (ID 2.5×20 cm length) and an isocratic mobile phase (80% acetonitrile: 20% water plus 0.1% v/v glacial acetic acid, flow rate 50 ml/min). Wavelength monitoring was at 278 nm. The peaks collected at 11–14 minutes, 19–21 minutes and 30–32 minutes were evaporated to dryness to yield the 5,6-dihydro-α-pyrone of formula (I) wherein R is $CO_2H$ (7.5 g), the fatty acid of formula (IIIa) (0.35 g) and the 5,6-dihydro-α-pyrone of formula (I) wherein R is $CH_3$ (0.9 g), respectively.

Physicochemical data for the three compounds are set out in Tables 1 to 3 below. Tables 2 and 3 show $^1H$ and $^{13}C$ NMR assignments respectively.

TABLE 14

| | 5,6-dihydro-α-pyrone of formula (I) | | fatty Acid of formula |
|---|---|---|---|
| | R is $CO_2H$ | R is $CH_3$ | (IIIa) |
| DCI-MS (m/z) | 391 $(MH)^+$ | 361 $(MH)^+$ | 225 $(NH)^+$ |
| Molecular formula | $C_{22}H_{30}O_6$ | $C_{22}H_{32}O_4$ | $C_{14}H_{24}O_2$ |
| $UV\lambda_{max}$nm | 206, 276 | 204, 274 | 265 |
| IR $(KBr)ucm^{-1}$ | 3391, 2960, 2928, 2855, 1717, 1620, 1570, 1396, 1285, 1250, 1161, 1024, 980. | 3390, 2960, 2929, 1720, 1615, 1560, 1250, 1180, 1010, 980. | 2900, 2685, 2589 1687, 1618, 1459 1417, 1285, 1207 1028, 984, 940, 952, 700 |

TABLE 2

| | †δH/ppm in MeOH-d4 | | |
|---|---|---|---|
| | 5,6-dihydro-α-pyrone of formula (I) | | Fatty Acid of |
| Position | R is $CO_2H$ | R is $CH_3$ | formula (IIIa)* |
| 2 | | | |
| 3 | 6.35 (1H, d, 9.7) | 6.29 (1H, d, 9.8) | |
| 4 | 7.21 (1H, dd, 9.7, 5.6) | 7.18 (1H, dd, 9.8, 5.6) | |
| 5 | 5.64 (1H, dd, 5.6, 3.0) | 5.48 (1H, dd, 5.6, 3.1) | |
| 6 | 5.49 (1H, m) | 5.19 (1H, ddq, 7.2, 3.0, 0.9) | |
| 7 | 6.91 (1H, dd, 15.7, 5.0) | 5.72 (1H, ddq, 15.4, 7.2, 1.7) | |
| 8 | 6.32 (1H, dd, 15.7, 1.8) | 6.05 (1H, dqd, 15.4, 6.6, 1.1) | |
| 9 | | 1.84 (3H, ddd, 6.8, 1.7, 0.8) | |
| 1' | | | |
| 1'-OH | | | 11.70 (1H, br s) |
| 2' | 5.88 (1H, d, 15.6) | 5.95 (1H, dd, 15.7, 0.6) | 5.77 (1H, d, 15.6) |
| 3' | 7.41 (1H, dd, 15.6, 0.6) | 7.41 (1H, dd, 15.6, 0.8) | 7.39 (1H, d, 15.6) |
| 4' | | | |
| 5' | 5.83 (1H, br d, 9.8) | 5.83 (1H, br d, 9.2) | 5.72 (1H, d, 9.8) |
| 6' | 2.66 (1H, m) | 2.65 (1H, m) | 2.53 (1H, m) |
| 7'–11' | 1.3–1.5 (10H, m) | 1.4 (10H, m) | 1.2–1.4 (10H, m) |
| 12' | 0.97 (3H, t, 6.9) | 0.95 (3H, t, 6.9) | 0.87 (3H, t, 6.7) |
| 13' | 1.87 (3H, d, 1.1) | 1.81 (3H, d, 1.2) | 1.78 (3H, d, 0.8) |
| 14' | 1.08 (3H, d, 6.6) | 1.09 (3H, d, 6.6) | 0.98 (3H, d, 6.6) |

*values obtained in $CDCl_2$
†The J values are in parenthesis (Hz)

TABLE 3

| | δC/ppm in MeOH-d4 | | |
|---|---|---|---|
| | 5,6-dihydro-α-pyrone of formula (I) | | Fatty Acid of formula |
| Position | R is $CO_2H$ | R is $CH_3$ | (IIIa) |
| 2 | 164.6 | 165.5 | |
| 3 | 125.6 | 126.1 | |
| 4 | 143.4 | 143.4 | |

TABLE 3-continued

| | $\delta C$/ppm in MeOH-d4 | | |
|---|---|---|---|
| | 5,6-dihydro-α-pyrone of formula (I) | | Fatty Acid of formula |
| Position | R is $CO_2H$ | R is $CH_3$ | (IIIa) |
| 5 | 64.9 | 65.6 | |
| 6 | 79.6 | 81.4 | |
| 7 | 139.6 | 125.5 | |
| 8 | 128.2 | 138.8 | |
| 9 | 170.7 | 18.2 | |
| 1' | 168.0 | 168.0 | 173.1 |
| 2' | 115.3 | 115.5 | 114.7 |
| 3' | 153.5 | 153.2 | 152.1 |
| 4' | 133.3 | 133.1 | 131.2 |
| 5' | 151.7 | 151.5 | 149.8 |
| 6' | 35.0 | 34.8 | 33.2 |
| 7' | 38.7 | 36.6 | 37.1 |
| 8' | 33.4 | 33.2 | 31.8 |
| 9' | 30.9 | 30.7 | 29.3 |
| 10' | 29.0 | 28.9 | 27.3 |
| 11' | 24.1 | 23.9 | 22.5 |
| 12' | 14.8 | 14.6 | 13.9 |
| 13' | 12.9 | 12.7 | 12.1 |
| 14' | 21.1 | 20.9 | 20.2 |

*values obtained in $CDCl_2$

EXAMPLE 3

Extraction and purification of the 5,6-dihydro-α-pyrones of formula (I) wherein one of $R^1$ and $R^2$ is H and the other is OH, and the fatty acids of formula (IIIb) from Phomopsis sp 22502.

The title compounds all possess a hydroxy substituent (as $R^1$ or $R^2$) and are therefore more polar analogues of the compounds of formulae (I) and (IIIa) produced as described in Example 2.

The title compounds were isolated from the broth of Example 1 as minor fermentation components, using purification methods similar to those described in Example 2.

Physicochemical data for the three compounds are set out in the following Tables 4 to 6. Tables 5 and 6 show $^1H$ and $^{13}C$ NMR assignments, respectively.

TABLE 4

| | Compound of formula (I) | | Fatty acid of formula (IIIb) | |
|---|---|---|---|---|
| | A ($R^1$ = H, $R^2$ = OH) | B ($R^1$ = OH, $R^2$ = H) | C ($R^1$ = H, $R^2$ = OH) | D ($R^1$ = OH, $R^2$ = H) |
| DCI-MS (m/Z) | 424 ($MNH_4+$) 407 (MH+) | 424 ($MNH_4+$) 407 (MH+) | 258 ($MNH_4+$) 240 (MH+) | 258 ($MNH_4+$) 240 (MH+) |
| Molecular formula | $C_{22}H_{10}O_7$ | $C_{22}H_{30}O_7$ | $C_{14}H_{24}O_3$ | $C_{14}H_{24}O_3$ |
| UV $\lambda_{max}$ nm | 203, 275 | 205, 274 | 267 | 266 |
| IR(KBr)u $cm^{-3}$ | 3444, 2956, 1723, 1621, 1289, 1249, 1159, 1107, 981 | 3400, 2900, 1714, 1620, 1286, 1247, 1156, 1106, 980 | 3255, 2900, 1694, 1627, 1382, 1285, 1193, 982 | 3363, 1692, 1622, 1285, 1198, 1029, 983 |

TABLE 5

| Position | $\delta H$/ppm in MeOH-d4 | | | |
|---|---|---|---|---|
| | A | B | C | D |
| 2 | | | | |
| 3 | 6.35 (1H, d, 9.8) | 6.35 (1H, d, 9.8) | | |
| 4 | 7.21 (1H, dd, 9.7, 5.7) | 7.21 (1H, dd, 9.8, 5.8) | | |
| 5 | 5.67 (1H, dd, 5.7, 3.0) | 5.67 (1H, dd, 6.3, 5.3) | | |
| 6 | 5.52 (1H, m) | 5.52 (1H, m) | | |
| 7 | 6.99 (1H, dd, 15.7, 4.5) | 6.98 (1H, dd, 15.7, 4.7) | | |
| 8 | 6.30 (1H, dd, 15.7, 1.8) | 6.31 (1H, dd, 15.7, 1.9) | | |
| 9 | | | | |
| 1' | | | | |
| 2' | 5.87 (1H, d, 15.5) | 5.87 (1H, d, 15.6) | 5.87 (1H, d, 15.6) | 5.85 (1H, d, 15.6) |
| 3' | 7.40 (1H, d, 15.3) | 7.40 (1H, d, 15.5 | 7.38 (1H, d, 15.9) | 7.40 (1H, d, 15.7) |
| 4' | | | | |
| 5' | 5.84 (1H, brd, 9.0) | 5.83 (1H, brd, 9.9) | 5.75 (1H, brd, 9.8) | 5.75 (1H, d, 9.8) |
| 6' | 2.67 (1H, m) | 2.67 (1H, m) | 2.68 (1H, m) | 2.65 (1H, m) |
| 7' | 1.3–1.5 (8H, m) | 1.3–1.55 (8H, m) | 1.35–1.6 (8H, m) | 1.4–1.6 (8H, m) |
| 8' | " | 1.3–1.55 (8H, m) | 1.35–1.6 (8H, m) | 1.4–1.6 (8H, m) |
| 9' | 3.50 (1H, m) | 1.3–1.55 (8H, m) | 3.52 (1H, m | 1.4–1.6 (8H, m) |
| 10' | 1.3–1.5 (8H, m) | 1.3–1.55 (8H, m) | 1.35–1.6 (8H, m) | 1.4–1.6 (8H, m) |
| 11' | " | 3.77 (1H, m) | 1.35–1.6 (8H, m) | 3.78 (1H, m) |
| 12' | 1.00 (3H, t, 7.4) | 1.23 (3H, d, 6.1) | 1.00 (3H, t, 7.4) | 1.20 (3H, d, 6.2) |
| 13' | 1.87 (3H, s) | 1.88 (3h, d, 1.0) | 1.90 (3H, d, 0.8) | 1.90 (3H, s) |
| 14' | 1.09 (3H, d, 6.6) | 1.08 (3H, d, 6.6) | 1.10 (3H, d, 6.6) | 1.10 (3H, d, 6.6) |

TABLE 6

| | $\delta C$/ppm in MeOH-d4 | | | |
|---|---|---|---|---|
| Position | A | B | C | D |
| 2 | 164.0 | 164.0 | | |
| 3 | 125.2 | 125.2 | | |
| 4 | 142.8 | 142.8 | | |
| 5 | 64.2 | 64.2 | | |
| 6 | 78.9 | 78.9 | | |
| 7 | 141.2 | 141.2 | | |
| 8 | 125.4 | 125.5 | | |
| 9 | 168.7 | 168.8 | | |
| 1' | 167.5 | 167.6 | 171.0 | 171.0 |
| 2' | 114.8 | 114.8 | 116.8 | 116.8 |
| 3' | 153.2 | 153.1 | 151.6 | 151.6 |
| 4' | 132.9 | 132.9 | 132.9 | 132.8 |
| 5' | 151.2 | 151.2 | 149.6 | 149.7 |
| 6' | 34.6 | 34.6 | 34.5 | 34.4 |
| 7' | 31.1 | 38.3 | 31.1 | 38.4 |
| 8' | 38.4 | 28.9 | 38.5 | 28.7 |
| 9' | 73.9 | 27.0 | 73.9 | 27.0 |
| 10' | 38.0 | 40.2 | 38.0 | 40.2 |
| 11' | 24.8 | 68.6 | 24.9 | 68.6 |
| 12' | 12.5 | 23.5 | 12.6 | 23.6 |
| 13' | 10.3 | 12.5 | 10.3 | 12.6 |
| 14' | 20.7 | 20.7 | 20.8 | 20.9 |

EXAMPLE 4
Batch Fermentation of Paecilomyces sp. 3527

Starting material of the strain Paecilomyces sp. 3527 was generated by suspending a mature slant culture, grown on MEA (2% malt extract, 1.5% agar), in 5 ml 10% aqueous glycerol. 1 ml of this suspension, in a 1.5 ml cryovial, comprises the starting material which was retrieved from storage at −135° C. A preculture was produced by aseptically placing 1 ml of starting material in a 250 ml baffled Erlenmeyer flask containing 40 ml of nutrient solution S2 shaken at 240 rpm for 3 days at 25° C.

An intermediate culture was generated by aseptically transferring the preculture to 2 L of nutrient solution S2 in a 3 L fermenter. The fermenter was agitated at 500 rpm, aerated at 0.5 vvm, and the temperature controlled at 25° C. for 3 days.

A production culture was generated by aseptically transferring an intermediate culture to a 75 L fermenter containing 50 L of nutrient solution P2. The production fermenter was stirred at 300 rpm, aerated at 0.5 vvm, and temperature controlled at 25° C. During the production fermentation the pH was uncontrolled and remained between 5.5 and 6.5. In addition the dissolved oxygen tension remained above 80%. After 5 days incubation the fermentation was stopped and the culture was harvested.

The solutions used were as follows, percentages being by weight:
Nutrient Solution S2: 1.5% glycerol, 1.5% soya bean peptone, 1% D-glucose, 0.5% malt extract, 0.3% NaCl, 0.1% $CaCO_3$, 0.1% Tween 80, 0.1% Junlon PW110 (Honeywell and Stein, Sutton, Surrey, U.K.) adjusted to pH 6
Nutrient Solution P2: 3.65% sucrose, 1.20% glutamic acid (sodium salt), 0.02% $K_2HPO_4$, 0.98% MES, 0.05% KCl, 0.1% Tween 80, 0.002% $MgSO_4$, 0.002% $CaCl_2$, 2% vitamin mix solution (see below), 0.5% trace elements solution (see below), adjusted to pH 6
vitamin mix solution: 0.0025% thiamine, 0.0025% riboflavin, 0.0025% pantothenate, 0.0025% nicotinic acid, 0.0025% pyridoxine, 0.0025% thioctic acid, 0.00025% folic acid, 0.00025% biotin, 0.00025% cyanocobalamin, 0.00025% p-amino benzoic acid, 0.005% vitamin K, 0.2% Tween 80.
trace elements solution: 0.17% $ZnSO_4$, 0.11% $FeSO_4$, 0.02% $MnSO_4$, 0.006% $H_3BO_3$, 0.012% $CuSO_4$, 0.005% $Na_2MoO_4$, 0.005% $CoCl_2$, 0.008% KI.

EXAMPLE 5
Extraction and Purification of the Phomalactone from Paecilomyces sp. 3527

The fermentation broth from Example 4 was harvested by filtration and the clarified filtrate was divided equally into 3 aliquots and each aliquot was back extracted batch wise with 10 L of hexane to remove non-polar impurities. The hexane extracts were separated and discarded. Each batch of filtrate was then back extracted with 2×8 L of ethyl acetate. The phomalactone and some impurities were extracted into the solvent while many of the more polar impurities remained in the aqueous phase. The ethyl acetate extracts were pooled and concentrated to dryness under reduced pressure and redissolved in 50 ml of ethyl acetate.

Purification was achieved by normal phase chromatography using a Biotage Flash 75 chromatography system and a Flash 75 KP-Sil silica (32–62 μm 60 Å) column (internal diameter 7.5×30 cm length) and an isocratic mobile phase (100% ethyl acetate, 200 ml/min flow rate). 1 L fractions were collected and analysed by thin layer chromatography using ethyl acetate as the developing solvent.

Phomalactone rich fractions (Rf 0.75) were pooled, evaporated to dryness under reduced pressure and subjected to further purification by preparative reversed phase HPLC using a Beckman 350 HPLC with a Shandon Hyper prep HS BOS C18 (100 Å 12 μm) column (internal diameter 10×30 cm length) and an isocratic mobile phase (85% water:15% acetonitrile, flow rate 170 ml/min). Wavelength monitoring was at 210 nm. The peak collected between 6–12 minutes was evaporated to dryness to yield the target phomalactone (6.0 g).

Physicochemical data for the phomalactone are set out in Tables 7 to 9 below. Tables 8 and 9 show $^1H$ and $^{13}C$ NMR assignments respectively.

TABLE 7

| | Phomalactone of formula (II) |
|---|---|
| DCI-MS (m/z) | 155 $(MH)^+$ |
| Molecular formula | $C_8H_{10}O_3$ |
| UV$\lambda_{max}$nm | 200 |
| IR (KBr)u$cm^{-1}$ | 3425, 2923, 2855, 1716, 1629, 1381, 1262, 1157, 1102, 1076, 1034, 969, 830. |

TABLE 8

| Position | †δH/ppm in $CDCl_3$ Phomalactone of formula (II) |
|---|---|
| 2 | |
| 3 | 6.12 (1H, d, 9.6) |
| 4 | 6.97 (1H, dd, 9.7, 5.2) |
| 5 | 4.21 (1H, dd, 5.2, 3.2) |
| 6 | 4.85 (1H, m) |
| 7 | 6.00 (1H, dqd, 15.3, 6.5, 1.0) |
| 8 | 5.75 (1H, ddq, 17.0, 6.9, 3.4) |
| 9 | 1.82 (3H, ddd, 6.1, 1.0) |

†The J values are in parenthesis (Hz)

TABLE 9

| Position | δC/ppm in $CDCl_3$ Phomalactone of formula (II) |
|---|---|
| 2 | 162.9 |
| 3 | 122.8 |
| 4 | 144.3 |
| 5 | 63.1 |
| 6 | 80.9 |
| 7 | 132.9 |
| 8 | 123.8 |
| 9 | 17.8 |

EXAMPLE 6
Synthesis of the 5,6-dihydro-α-pyrone of formula (I) wherein $R^1$ and $R^2$ are H and R is $CH_3$ by esterification of the phomalactone with the fatty acid of formula (IIIa).

A solution of the phomalactone (20 mg, 0.13 mmol 1 eq) in dry dichloromethane (2 ml) was added to a stirred solution of the fatty acid of formula (III) (29 mg, 0.13 mmol), 1-(3-dimethylaminopropyl)-3-ethylcarbodiimide hydrochloride (24.8 mg, 0.13 mmol, 1 eq) and dimethylaminopyridine (1 mg) in dry dichloromethane (5 ml) at −78° C. The reaction mixture was allowed to warm to room temperature and was stirred for a further 16 hours. The reaction mixture was washed with saturated ammonium chloride solution (3×5 ml), water (1×5 ml) and brine (1×5 ml). The organic extract was dried over $MgSO_4$, filtered and concentrated in vacuo yielding a yellow oil. Purification by preparative reversed phase HPLC yielded the 5,6-dihydro-α-pyrone of formula (I) wherein $R^1$ and $R^2$ are H and R is $CH_3$ (11.1 mg). HPLC, TLC, and $^1H$ NMR analysis showed that this product was identical to the isolated natural product.

EXAMPLE 7

TNP-α Release from U937 Cells

The effect of the compounds of the invention on TNF-α release was investigated using a known method (Lozanski, G. et al., (1992), J. Rheumatol; 19, 921–26).

The human histolytic lymphoma U937 cell line was obtained from a commercial source (ECACC, Salisbury, UK) and maintained in RPMI 1640 medium supplemented with 2 mM L-glutamine and 5% fetal bovine serum. The cells were pretreated with 25 ng/ml PMA for six hours and then exposed to dose ranges of the compound to be tested followed by the addition of 1 ng/ml LPS.

After 18 hours incubation at 37° C. with 5% $CO_2$ the cell culture supernatants were harvested and stored at −70° C., until required for determination of TNF-α secretion by Dissociation Enhanced Lanthanide Fluorescence Immuno Assay (DELFIA). The effect of the compounds on cell cytotoxicity was measured using the tetrazolium salt, XTT (2,3-bis[2-methoxy-4-nitro-5-sulphophenyl]-2H-tetrazolium-5-carboxanilide salt) and effects on protein synthesis were determined by investigation of [$^3$H] Leucine uptake.

In this test the compounds of the invention were found to inhibit TNF-α release at concentrations of from 10 to 0.1 μM (Table 10). At this concentration range, the compounds were not toxic and showed no effect on protein synthesis. The $IC_{50}$(μM) values for LPS-induced TNF production in U937 cells for the 5,6-dihydro-α-pyrones for formula (I) are given in Table 11.

EXAMPLE 8

IL-1 Release from Human Monocytes

The effect of the compounds of the invention on IL-Iβ release was investigated using a known method (Bakouche, O. et al., (1992), J. Immunol: 148, 84–91). Human monocytes were purified by elutriation from Buffy coats obtained from normal healthy donors after the separation of peripheral blood mononuclear cells (PBMC) on Lymphoprep. The freshly isolated monocytes were suspended in RPMI 1640 supplemented with 5% FBS and exposed to dose ranges of the compound to be tested followed by the addition of 1 ng/ml LPS. Cells were incubated for 18 hours at 37° C. with 5% $CO_2$ and the cell culture supernatants harvested and stored at −70° C. Effects on the production of IL-1β were determined using an ELISA.

The compounds of the invention were found to inhibit the release of IL-1β at concentrations of from 0.2 to 10 μM (Table 12). At this concentration range the compounds were not toxic to monocytes. The $IC_{50}$ (μM) values for LPS-induced IL-1β production for the 5,6-dihydro-α-pyrones of formula (I) are given in Table 11.

TABLE 10

Inhibition of TNF-α release

| | Concentration μM | % Inhibition of TNF-α |
| --- | --- | --- |
| R in formula (I) is $CO_2H$ | 8 | 107 |
| | 2 | 100 |
| | 0.5 | 77 |
| | 0.12 | 47 |
| R in formula (I) is $CH_3$ | 2.8 | 99 |
| | 0.7 | 90 |
| | 0.17 | 61 |
| | 0.04 | 20 |
| | 0.01 | 0.85 |

TABLE 11

$IC_{50}$s for inhibition of LPS-induced cytokine production by the 5,6-dihydro-α-pyrones of formula (I)

| | | $IC_{50}$ (μM) | |
| --- | --- | --- | --- |
| $R^1$, $R^2$ in formula (I) | R in Formula (I) | LPS-induced TNF production in U937 cells | LPS-induced IL-β production (monocytes) |
| H, H | $CO_2H$ | 2 | 2 † |
| H, H | $CH_3$ | 0.08 | 0.19 |
| H, OH | $CO_2H$ | 32 | — |
| OH, H | $CO_2H$ | 31 | — |

TABLE 12

Inhibition of the release of Il-1β

| | Concentration μM | % Inhibition of IL-1β |
| --- | --- | --- |
| R in formula (I) is $CO_2H$ | 20 | 99 |
| | 2 | 81.5 |
| | 0.5 | 14 |
| R in formula (I) is $CH_3$ | 5.5 | 88 |
| | 1.1 | 72 |
| | 0.22 | 41 |
| | 0.044 | 23 |

What is claimed is:

1. A 5,6-dihydro-α-pyrone of formula (I)

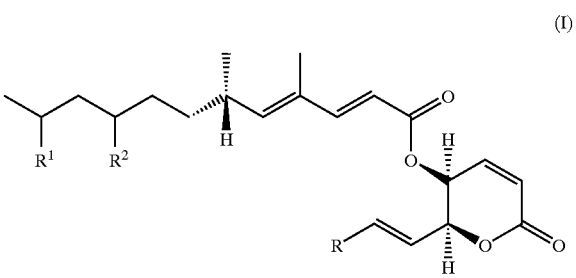

(I)

wherein R is $CO_2H$ or $CH_3$ and each of $R^1$ and $R^2$ is H; or R is $CO_2H$, one of $R^1$ and $R^2$ is H and the other is OH; or, when R is $CO_2H$, a pharmaceutically or veterinarily acceptable salt thereof.

2. A process for the preparation of a 5,6-dihydro-α-pyrone of formula (I) as defined in claim 1 or a pharmaceutically or veterinarily acceptable salt thereof, which process comprises:

(i) fermenting, in a source of carbon, nitrogen and inorganic salts, fungal strain Phomopsis sp. 22502 (CBS 313.96) or a mutant thereof which produces a said 5,6-dihydro-α-pyrone;

(ii) isolating a said 5,6-dihydro-α-pyrone from the fermentation broth; and (iii) if desired when the isolated said 5,6-dihydro-α-pyrone is the compound of formula (I) wherein R is $CO_2H$, converting the said 5,6-dihydro-α-pyrone into a pharmaceutically or veterinarily acceptable salt thereof.

3. A process for the preparation of a 5,6-dihydro-α-pyrone of formula (I), as defined in claim 1, wherein R is $CH_3$, which process comprises esterifying the phomalactone of formula (II):

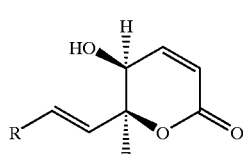

(II)

with a fatty acid of formula (IIIa):

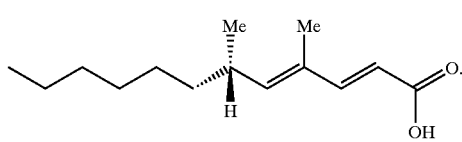

(IIIa)

4. A pharmaceutical or veterinary composition comprising a pharmaceutically or veterinarily acceptable carrier or diluent and, as active ingredient, a compound as claimed in claim 1.

5. A method of treating a patient in need of a cytokine production inhibitor, which method comprises administering thereto a therapeutically effective amount of a compound as defined in claim 1.

6. A method according to claim 5 wherein the cytokine production inhibitor is an IL-1 production inhibitor.

7. A method of treating a clinical condition requiring immunosuppression, which method comprises administering to a patient in need thereof a therapeutically effective amount of a compound as defined in claim 1.

8. A method according to claim 7 wherein said clinical condition is an immunoinflammatory condition.

9. A method according to claim 8 wherein said immunoinflammatory condition is selected from the group consisting of rheumatoid arthritis, osteoarthritis, septic shock, psoriasis, atherosclerosis, inflammatory bowel disease, Crohn's disease and asthma.

10. A method according to claim 7 wherein said clinical condition is a central nervous system disorder.

11. A method according to claim 10 wherein said central nervous system disorder is selected from the group consisting of encephalomyelitis and Alzheimer's disease.

* * * * *